United States Patent [19]

Meyer et al.

[11] Patent Number: 5,093,509
[45] Date of Patent: Mar. 3, 1992

[54] REMOVAL OF TRACE QUANTITIES OF MOLYBDENUM

[75] Inventors: Robert A. Meyer, Ballwin, Mo.; Edward T. Marquis, Austin, Tex.

[73] Assignee: Texaco Chemical Company, White Plains, N.Y.

[21] Appl. No.: 702,523

[22] Filed: May 20, 1991

[51] Int. Cl.$^5$ .............. C07F 11/00; C07D 301/19
[52] U.S. Cl. ........................... 556/57; 549/529; 423/53; 423/55; 423/56; 502/24; 502/26; 502/53; 502/54
[58] Field of Search ............... 556/57; 549/529; 423/53, 55, 56; 502/24, 26, 53, 54

[56] References Cited

U.S. PATENT DOCUMENTS

| | | | |
|---|---|---|---|
| 3,351,635 | 11/1967 | Kollar | 260/348.5 |
| 3,418,340 | 12/1968 | Russell | 260/348.5 |
| 3,480,563 | 11/1969 | Bonetti et al. | 252/431 |
| 3,573,226 | 3/1971 | Sorgenti | 252/431 |
| 3,819,663 | 6/1974 | Levine et al. | 260/348.5 L |
| 3,931,044 | 1/1976 | Maurin | 252/414 |
| 4,455,283 | 6/1984 | Sweed | 423/53 |
| 4,650,886 | 3/1987 | Marquis et al. | 556/57 |
| 4,654,427 | 3/1987 | Marquis et al. | 556/57 |

FOREIGN PATENT DOCUMENTS 1191940  5/1970  United Kingdom ............ 502/24

Primary Examiner—Jose G. Dees
Assistant Examiner—Porfirio Nazario
Attorney, Agent, or Firm—Jack H. Park; Kenneth R. Priem; Carl G. Ries

[57] ABSTRACT

An epoxidation reaction product formed by the molybdenum catalyzed reaction of propylene with tertiary butyl hydroperoxide to provide propylene oxide and tertiary butyl alcohol is separated by distillation into a propylene fraction, a propylene oxide fraction, a tertiary butyl alcohol fraction and a heavy liquid distillation fraction composed primarily of tertiary butyl hydroperoxide, tertiary butyl alcohol, dissolved molybdenum catalyst, and impurities including lower aliphatic $C_1$–$C_4$ carboxylic acids, and the dissolved molybdenum content of the heavy distillation fraction is adjusted to about 300 to 500 ppm of dissolved molybdenum, if necessary, by treatment with a precipitating agent and contacted with a solid adsorbent consisting essentially of a synthetic, porous, high surface area amorphous magnesium silicate.

4 Claims, 1 Drawing Sheet

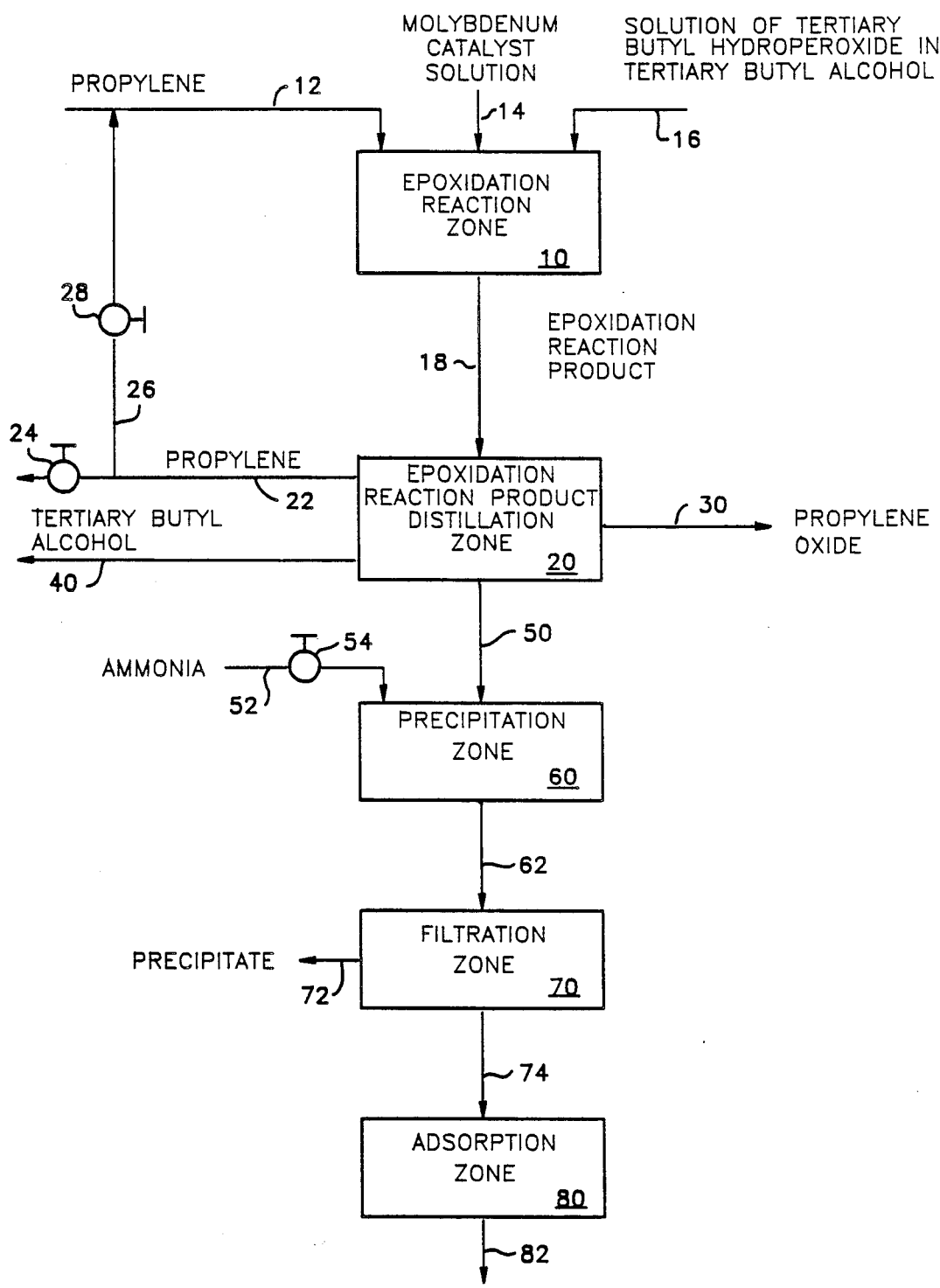

REMOVAL OF TRACE QUANTITIES OF MOLYBDENUM

BACKGROUND OF THE INVENTION

1. Field of the Invention

This invention relates to an improvement in the process for resolving the reaction mixture that is formed in preparing propylene oxide and tertiary butyl alcohol by reacting propylene with tertiary butyl hydroperoxide in solution in tertiary butyl alcohol in the presence of a soluble molybdenum catalyst. More particularly, this invention is directed to substantially removing molybdenum from the reaction mixture.

Molybdenum compounds are somewhat toxic to livestock and, therefore, solutions containing molybdenum must be handled with care. Also, the presence of molybdenum in liquid by-products presents a disposal problem because of the limited toxicity of molybdenum to livestock.

The epoxidation reaction mixture that is formed when propylene is reacted with tertiary butyl hydroperoxide in solution in tertiary butyl alcohol in the presence of a soluble molybdenum epoxidation catalyst will normally comprise unreacted propylene, propylene oxide, tertiary butyl alcohol, unreacted tertiary butyl hydroperoxide, the soluble molybdenum catalyst and impurities, including $C_1$ to $C_4$ lower aliphatic carboxylic acids. The reaction mixture is usually separated by distillation into plurality of fractions including a recycle propylene fraction, a propylene oxide product fraction, a tertiary butyl alcohol product fraction and a heavy liquid distillation fraction containing tertiary butyl alcohol, unreacted tertiary butyl hydroperoxide and impurities, including substantially all of the dissolved molybdenum catalyst and a portion of the lower aliphatic carboxylic acid impurities.

In accordance with the present invention, the heavy liquid distillation fraction or a fraction thereof containing from about 50 to 500 ppm of dissolved molybdenum is passed through a bed of a solid adsorbent consisting essen-tially of a synthetic, porous, high surface area amorphous magnesium silicate in order to substantially completely remove the dissolved molybdenum and to provide a liquid eluate containing not more than about 20 ppm of dissolved molybdenum.

The heavy liquid distillation fraction may initially contain as little as 0.03 wt. % (300 ppm) of dissolved molybdenum, but will normally contain from about 0.06 to about 0.6 wt. % (about 600 to about 6,000 ppm) of dissolved molybdenum. When the heavy liquid distillation fraction contains from about 300 to 500 ppm of dissolved molybdenum, it may be treated directly with the bed of synthetic, porous, high surface area amorphous magnesium silicate in order to substantially completely remove the dissolved molybdenum and to provide a liquid eluate containing not more than about 20 ppm of dissolved molybdenum. However, if the heavy liquid distillation fraction contains more than about 500 ppm of dissolved molybdenum, such as about 600 to about 6,000 ppm, as is usually the case, in accordance with a preferred embodiment of the present invention, the heavy liquid distillation fraction is first treated, non-catalytically, with a precipitating agent such as ammonia in a precipitation zone to form a precipitate comprising most of the dissolved molybdenum and from which a liquid fraction, such as a filtrate, can be recovered (e.g., by filtration) which will contain from about 50 to 500 ppm of dissolved molybdenum and which is charged, as feed, to the adsorption zone for treatment with the bed of synthetic, porous, high surface area amorphous magnesium silicate in order to substantially completely remove the dissolved molybdenum and to provide a liquid eluate containing not more than about 20 ppm of dissolved molybdenum.

The separate precipitate will comprise a concentrated solid molybdenum product that may be processed for the recovery of molybdenum. The precipitate will contain substantially all of the molybdenum present in the reaction mixture and, as a consequence, the thus-treated molybdenum fraction will pose a lesser environmental problem and can be disposed of more easily.

2. Prior Art

It is known to react propylene with tertiary butyl hy-droperoxide in the presence of a soluble molybdenum catalyst to provide a reaction product comprising propylene oxide and tertiary butyl alcohol. See, for example, Kollar U.S. Pat. No. 3,350,422, Kollar U.S. Pat. No. 3,351,635, and Russell U.S. Pat. No. 3,418,340.

It is also known to prepare soluble molybdenum catalysts to catalyze the reaction as disclosed, for example, in Bonetti et al. U.S. Pat. No. 3,480,563, Shum et al. U.S. Pat. No. 4,607,113, Marquis et al. U.S. Pat. No. 4,626,596, Marquis et al. U.S. Pat. No. 4,650,886, Marquis et al. U.S. Pat. No. 4,703,027, etc.

Kollar U.S. Pat. No. 3,860,662 is directed to an improvement in his basic process relating to the recovery of alcohols from the reaction product, which product is stated to be of an acidic nature, wherein a basic material such as an alkali metal or alkaline earth metal compound is added to the reaction mixture. Kollar U.S. Pat. No. 3,947,500 discloses a method for treating the reaction product formed by the reaction of an organic hydroperoxide with an olefin wherein an organic alcohol is formed as a by-product. It is stated that the alcohol tends to dehydrate and that to at least partially overcome this problem the oxidation reaction product is treated with an alkali metal or an alkaline earth metal compound. Kollar states that the alkali metal or alkaline earth metal compound can be added to the epoxidation reactor or to the reaction product.

Sorgenti U.S. Pat. No. 3,573,226 discloses a method wherein a molybdenum-containing catalyst solution is prepared by incorporating metallic molybdenum into the distillate bottoms fraction of an epoxidation reaction product followed by heating of the resultant mixture in order to form a soluble molybdenum-containing reaction product which can be used to catalyze the epoxidation reaction.

The molybdenum-catalyzed epoxidation of alpha olefins and alpha substituted olefins with hydroperoxides less stable than tertiary butyl hydroperoxide may be accomplished according to U.S. Pat. No. 3,862,961 to Sheng, et al. by employing a critical amount of a stabilizing agent consist-ing of a $C_3$ to $C_9$ secondary or tertiary monohydric alcohol, such as tertiary butyl alcohol. Citric acid is used to minimize the iron-catalyzed decomposition of the organic hydroperoxide without adversely affecting the reaction between the hydroperoxide and the olefin. A similar oxirane producing process is disclosed in Herzog in U.S. Pat. No. 3,928,393. The inventors in U.S. Pat. No. 4,217,287 discovered that if barium oxide is present in the reaction mixture, the catalytic epoxidation of olefins with organic hydroperoxides can be successfully carried out with good selectivity to the epoxide based on hydroperoxide converted when a relatively low olefin to hydroperoxide mole ratio is used. The alpha-olefinically unsaturated compound should be added incrementally to the organic hydroperoxide.

Maurin U.S. Pat. No. 3,931,044 is directed to a method for recovering molybdenum catalyst values from a peroxidation reaction product for recycle. Maurin discloses one of three techniques. In accordance with the first embodiment, the residue fraction is calcined to provide molybdenum trioxide which is then used to prepare a soluble molybdenum compound by reaction with aqueous ammonia. In a second embodiment, the molybdenum-containing fraction is treated with aqueous ammonia without calcining to form an ammonium molybdate which is treated with a polyalcohol to give a molybdic ester. In a third embodiment, the molybdenum-containing fraction is treated with gaseous ammonia in order to form an ammonium molybdate precipitate which can be recovered by filtration.

Harvey U.S. Pat. No. 3,449,217 is directed to a process for the recovery of tertiary butyl hydroperoxide from a mixture comprising tertiary butyl hydroperoxide, tertiary butyl alcohol and organic acids and esters result-ing from the liquid phase oxidation of isobutane by a pro-cess which minimizes hydroperoxide decomposition. This is done by accomplishing the distillation while the product has an effective pH of below about 9. The patentee teaches the treatment of the reactor effluent with a neutralizing agent such as an alkali metal or an alkaline earth metal hydroxide.

Levine U.S. Pat. No. 3,819,663 is directed to a method for treating a heavy distillation fraction of this nature in order to recover the molybdenum in the concentrated bottoms fraction for recycle to the epoxidation reaction zone as makeup catalyst.

Levine conducts his wiped-film evaporation process under conditions including a temperature of about 550°-650° F. (about 273° to about 330° C.) at atmospheric pressure to obtain his desired residual fraction for recycle as catalyst makeup and a distillate fraction comprising about 85% or more of the heavy distillation fraction. Levine states that the distillate fraction that is thus obtained can be used as a furnace fuel or can be worked up for recovery of the indi-vidual components contained therein. However, Levine et al. does not contain any teaching as to how the individual components in the fraction would be obtained.

U.S. Pat. No. 4,079,116 discloses a process for producing ammonium heptamolybdate from a molybdenum oxide concentrate involving, as one of the steps, the treatment of a filtrate with a cation exchange resin in order to recover molybdenum contained in the filtrate.

Su U.S. Pat. No. 4,328,191 discloses a process for recovering molybdenum from the catalyst residue derived from an olefin epoxidation process wherein the residue is treated with an oxidizing agent such as nitric acid, hydrogen peroxide, sodium hypochlorite, etc., to form an aqueous solution of molybdenum compounds that can be recovered by filtration. The aqueous filtrate contains organic residues that are removed by passing the filtrate through a bed of adsorbent, namely charcoal, to remove the organic residues. Thereafter, molybdenum is recovered from the thus-treated filtrate.

In Canavesi U.S. Pat. No. 4,331,567, a process is disclosed that is directed to the preparation of an olefin epoxidation catalyst containing both ferric and molybdenum salts, a processing step is employed wherein a filtrate formed during a filtration step is treated with an anionic exchange resin in order to recover molybdenum contained in the filtrate.

Canavasi U.S. Pat. No. 4,401,631 discloses a process for recovering molybdenum from catalyst residues from an olefin epoxidation process wherein the spent catalyst, in the oxide form, is treated with an aqueous alkali metal hydroxide to solubilize the molybdenum in the form of an alkali metal molybdate and is then treated with a strong cationic exchange resin to convert the molybdate to molybdic acid.

A process for recovering the molybdenum contained in an olefin epoxidation catalyst is disclosed in Moore et al. U.S. Pat. No. 4,405,572 wherein a catalyst-containing residue fraction is treated with an aqueous alkaline material to form a molybdenum-containing aqueous phase from which the molybdenum can be recovered by acidification and precipitation or by treatment with a cation exchange resin.

SUMMARY OF THE INVENTION

In accordance with the present invention, a heavy liquid distillation fraction comprising tertiary butyl hyroperoxide, tertiary butyl alcohol and impurities including about 300 to about 500 ppm of dissolved molybdenum and lower aliphatic carboxylic acids resulting from the removal of propylene, propylene oxide and tertiary butyl alcohol from an epoxidation reaction product, or a fraction thereof, as hereafter described, is passed through a bed of a solid adsorbent consisting essentially of a synthetic, porous, high surface area amorphous magnesium silicate in order to substantially completely remove the dissolved molybdenum and to provide a liquid eluate containing not more than about 20 ppm of dissolved molybdenum.

However, if the heavy liquid distillation fraction contains more than about 500 ppm of dissolved molybdenum, such as about 600 to about 6,000 ppm, as is usually the case, in accordance with a preferred embodiment of the present invention, the heavy liquid distillation fraction is first treated with a precipitating agent such as ammonia in a precipitation zone to form a precipitate comprising most of the dissolved molybdenum.

The precipitation zone which may suitably comprise a reactor, such as an autoclave, provided with suitable agitating means (e.g., an impeller), temperature control means such as a jacket or coils through which a liquid heat exchange medium can be circulated, charge lines for the heavy distillation fraction and for the ammonia and a dis-charge line for withdrawal of the treated product. Within the precipitation zone the ammonia will react with the molyb-denum compounds present in the heavy distillation fraction to form a reaction product comprising a molybdenum-containing precipitate that can be withdrawn from the precipitation zone. The precipitate can be removed in any desired manner in a precipitate removal zone (e.g., by filtration, cen-trifugation, etc.). The precipitate can be recovered for disposal in any suitable environmentally acceptable manner, such as for example by treatment in a metals-reclaiming plant for the recovery of the molybdenum.

The filtrate fraction may then be passed through a bed of a solid adsorbent consisting essentially of a synthetic, porous, high surface area amorphous magnesium silicate in order to substantially completely remove the dissolved molybdenum and to provide a liquid eluate containing not more than about 20 ppm of dissolved molybdenum.

When the precipitating agent to be used is ammonia, the non-catalytic precipitation reaction may be conducted in the manner described in greater detail in co-pending Marquis et al. U.S. patent application entitled: "Molybdenum Recovery" (07/702,521), filed of an even date herewith.

Since the heavy distillation fraction will normally contain less than about 1 wt. % of water, when ammonia is used as the precipitating agent, ammonia should be used, as such, rather than in the form of an aqueous ammoniacal solution.

The ammonia should preferably be used in an amount which is equivalent to the amount of molybdenum in the heavy distillation fraction and, preferably, an excess of ammonia will be used, such as about 1 to about 200 moles of ammonia per gram atom of molybdenum present in the heavy distillation fraction. Preferably, the heavy distillation fraction is saturated with ammonia.

The precipitation reaction can be conducted under ambient conditions of temperature and pressure, although somewhat higher temperatures and pressures may be used, if desired, such as temperatures within the range of about 20° to 250° C. and pressures within the range of about 0 to 3,000 psig. The contact time should be sufficient to insure that the precipitation reaction goes to completion (e.g., 0.2 to 2 hours).

After the precipitation reaction is completed, the mixture of precipitate and treated heavy distillation fraction is withdrawn from the precipitation zone for removal of the precipitate. The precipitate can be removed in any desired manner, e.g., filtration, centrifugation, evaporation, etc. Since the precipitate constitutes only a minor amount of the mixture of precipitate and treated heavy distillation fraction, filtration is preferred.

In accordance with the present invention, the filtrate obtained from the precipitation step is passed through a bed of a solid adsorbent consisting essentially of a synthetic, porous, high surface area amorphous magnesium silicate, such as one of the commercial products sold by The Dallas Group of America under the trade name Magnesol (e.g., Magnasol or Magnasol Code XL). The adsorption step is suitably conducted at temperatures from ambient to 100° C. and pressures from atmospheric to 1000 psig. and conducted so that the solution being treated is in intimate contact with the absorbent for a period of about an hour.

The precipitate, which will normally contain about 40 to about 58 wt. % of molybdenum can be disposed of in an environmentally acceptable manner. For example, it can be used as a feedstock in a metals-reclaiming plant or used as a raw material for the preparation of an additional amount of fresh molybdenum catalyst solution.

BACKGROUND INFORMATION

When propylene is reacted with tertiary butyl hydroperoxide in solution in tertiary butyl alcohol in an epoxidation reaction zone in the presence of a soluble molybdenum catalyst to form propylene oxide and additional tertiary butyl alcohol, an epoxidation reaction mixture is formed which will contain not only unreacted feed components and the desired propylene oxide and tertiary butyl alcohol, but also impurities including the dissolved molybdenum catalyst, oxygen-containing impurities such as ditertiary butyl peroxide, lower aliphatic $C_1$ to $C_4$ carboxylic acids such as formic acid, acetic acid, isobutyric acid, etc., alcohols such as methanol, isopropyl alcohol, tertiary butyl alcohol, etc., esters such as methyl formate, methyl acetate, methyl isobutyrate, etc., ketones such as acetone, etc., aldehydes such as isobutyraldehyde, etc., and hydrocarbon impurities resulting from undesired side reactions of the propylene, such as hydrocarbons containing 6 or more carbon atoms.

Although most of the impurities are originally present in the epoxidation reaction mixture in trace quantities, as the epoxidation reaction mixture is resolved by distillation into a propylene recycle fraction, a propylene oxide product fraction and a tertiary butyl alcohol product fraction, all of which are distillate fractions, the impurities are progressively concentrated in a heavier distillation fraction, such as a distillation fraction having the composition generally set forth in Table I.

TABLE I

| COMPOSITION OF HEAVY DISTILLATION FRACTIONS | |
| --- | --- |
| Component | Concentration, Wt. % |
| Impurities lighter than TBA | 0.1–2 |
| Tertiary butyl alcohol | 70–90 |
| Impurities heavier than TBA but lighter than TBHP | 1–4 |
| Tertiary butyl hydroperoxide | 2–20 |
| Impurities heavier than TBHP | 3–12 |
| Molybdenum concentration | 500–5,000 ppm |

BRIEF DESCRIPTION OF THE DRAWING

In the drawing, the figure is a schematic drawing of a preferred reaction and purification sequence that may be used in the practice of the present invention.

DESCRIPTION OF THE PREFERRED EMBODIMENT

Turning now to the drawing, there is shown a schematic flowsheet illustrating a preferred method of practicing the process of the present invention.

An epoxidation reaction zone 10 is provided and propyl-ene is charged thereto by a line 12 together with a soluble molybdenum catalyst charged by a line 14. A solution of tertiary butyl hydroperoxide in tertiary butyl alcohol is charged by a line 16.

The epoxidation reaction is an epoxidation reaction of the type disclosed by Kollar U.S. Pat. No. 3,351,653 as further elaborated upon, for example, in British patent specification No. 1,298,253 wherein propylene is reacted with tertiary butyl hydroperoxide under reaction conditions including a reaction temperature within the range of about 180° to about 300° F., a pressure of about 300 to about 1000 psig. and, more preferably, a temperature of about 220° F. to about 280° F. and a pressure of about 500 to about 800 psig. As another example, the epoxidation of propylene with tertiary butyl hydroperoxide in solution in tertiary butyl alcohol in the presence of a soluble molybdenum catalyst is disclosed in Marquis et al. U.S. Pat. No. 4,891,437. See also, Marquis et al. U.S. Pat. No. 4,845,251.

The soluble molybdenum catalyst charged to the epoxidation reaction zone by the line 14 may be an epoxidation catalyst of the type known in the art such as those disclosed by the Kollar patent or the British patent or by Marquis et al. U.S. Pat. No. 4,626,596, U.S. Pat. No. 4,650,886, U.S. Pat. No. 4,654,427, U.S. Pat. No. 4,703,027, or U.S. Pat. No. 4,758,681. The Marquis et al. patents are directed to molybdenum/alkanol complexes such as solutions of molybdenum compounds in ethylene glycol which contain a high concentration of molybdenum and are particularly useful as catalysts in the epoxidation reaction. Marquis et al. teach, for example, the epoxidation of propylene with tertiary butyl hydroperoxide with their catalyst under epoxidation conditions including a temperature of 50 to 180° C. and a use of propylene to tertiary butyl hydroperoxide ratios within the range of about 0.9:1 to about 3.0:1.

Suitably, the tertiary butyl hydroperoxide that is charged to the epoxidation reaction zone 10 by way of line 16 is about a 40 to about 75 wt. % solution of tertiary butyl hydroperoxide in tertiary butyl alcohol. The catalyst is charged to the epoxidation reaction zone 10 by the charge line 14 in an amount such as to provide from about 50 to about 1000 ppm of molybdenum, based on the total of the reactants charged and, more preferably, from about 200 to 600 ppm. The reaction is preferably conducted at superatmospheric pressure such as a pressure of about 300 to 1000 psig.

When the reaction is conducted on a continuous basis, as illustrated in the drawing, the feed materials are charged to the epoxidation reaction zone 10 through the lines 12, 14 and 16 at rates sufficient to maintain the desired concentration of reactants and an equivalent volume of epoxidation reaction mixture is withdrawn from the epoxidation reaction zone 10 by way of a discharge line 18. The reaction product discharged by the line 18 will normally comprise unreacted propylene, a minor amount of unreacted tertiary butyl hydroperoxide, propylene oxide, tertiary butyl alcohol, including tertiary butyl alcohol formed by the reaction of the tertiary butyl hydroperoxide with propylene, the molybdenum catalyst and impurities such as propane, propionaldehyde, acetone, methanol, isopropanol, water, acetaldehyde, methyl formate, acetic acid, formic acid, isobutyric acid, hydrocarbons containing 6 or more carbon atoms and high boiling residue components.

The reaction product 18 is charged to an epoxidation reaction product distillation zone 20 where it is separated by distillation into desired fractions in accordance with methods known to those skilled in the art. For example, the distillation sequence disclosed in British Patent No. 1,298,253 may be used.

One of the distillate products that is recovered in the zone 20 is a propylene fraction which is discharged by a line 22 controlled by valve 24 and provided with a branch line 26 controlled by a valve 28 in order to permit the recycle of unreacted propylene to the epoxidation reaction zone 10 through the propylene charge line 12.

Another distillate fraction that is obtained is a propylene oxide product fraction 30 which is discharged by the line 30.

The propylene oxide fraction may be purified in a propylene oxide purification zone (not shown) by known techniques such as, for example, those disclosed in Burnes et al. U.S. Pat. No. 3,715,284, Schmidt et al. U.S. Pat. No. 3,909,366, Schmidt U.S. Pat. No. 3,881,996, Jubin U.S. Pat. No. 3,607,669, Schmidt U.S. Pat. No. 3,843,488 or Schmidt U.S. Pat. No. 4,140,588.

Another product that is recovered from the epoxidation reaction product distillation zone 20 is a tertiary butyl alcohol distillate product 40 which may be further purified, if desired, to remove oxygenated impurities therefrom by catalytic treatment as disclosed, for example, in Sanderson et al U.S. Pat. No. 4,704,482, Sanderson et al. U.S. Pat. No. 4,705,903 or Sanderson et al. U.S. Pat. No. 4,742,149.

A heavy distillation fraction 50, usually a bottoms fraction, is also discharged from the epoxidation reaction product distillation zone 20. As described by Levine U.S. Pat. No. 3,819,663 and Sweed U.S. Pat. No. 4,455,283, the heavy distillation fraction will contain substantially all of the molybdenum catalyst initially charged to the epoxidation reaction zone 10 by way of the line 14. The heavy distillation fraction 50 will contain other products such as tertiary butyl hydroperoxide, tertiary butyl alcohol and impurities including oxygenates lighter than tertiary butyl alcohol such as acetaldehyde, acetone, isopropyl alco-hol, etc., oxygenates heavier than tertiary butyl alcohol but lighter than tertiary butyl hydroperoxide, and residue components heavier than tertiary butyl hydroperoxide such as propylene glycol tertiary butyl ethers, etc. As indicated, the heavy distillation fraction 50 will also contain carboxylic acids such as formic acid, acetic acid and isobutyric acid.

Although the molybdenum catalyst is present in the epoxidation reaction zone 10 in an amount in the range of about 50 to 1,000 ppm, and usually 200 to 600 ppm, it is progressively concentrated in the epoxidation reaction product distillation zone 20 and is normally present in the heavy distillation fraction 50 in an amount in the range of about 300 to 6,000 ppm or more.

The molybdenum-contaminated heavy distillation fraction 50, in accordance with the present invention, is charged to a precipitation zone 60 which may comprise a reaction vessel such as an autoclave which is equipped with suitable agita-tion means (e.g., an impeller) and suitable temperature control means such as an external jacket or internal coils through which a heat exchange medium can be circulated. Within the precipitation zone the heavy distillation frac-tion 50 is brought into contact with a precipitating agent such as ammonia which may be charged by a line 52 controlled by a valve 54. A molar excess of ammonia should be used, as described above.

When ammonia is used (e.g., by opening valve 54) it is preferably used in the form of anhydrous ammonia in order to minimize the water content of the heavy distillation fraction 50. The ammonia is suitably brought into contact with the heavy distillation fraction 50 under ambient temperature and pressure conditions, although higher temperatures and/or pressures may be used, such as temperatures within the range of about 20° to 250° C. and pressures within the range of 0 to about 3,000 psig. The contact time should be sufficient to ensure as complete a reaction of the ammonia with the molybdenum as is reasonably possible and to ensure substantially complete precipitation of the product, such as a contact time of about 0.2 to 2 hours.

The thus-formed slurry of precipitate in the treated heavy distillation fraction 50 is discharged from the precipitation zone 60 by a slurry discharge line 62 leading to a precipitate separating zone, such as a filtration zone 70 where the slurry is resolved into a precipitate that is removed by a discharge line 72 and a filtrate fraction that is discharged by a filtrate discharge line 74.

In accordance with the present invention, the filtrate fraction 74, which will normally contain from about 50 to about 500 ppm of molybdenum will be charged to an adsorption zone 80 containing a bed of a solid adsorbent consisting essentially of a synthetic, porous, high surface area amorphous magnesium silicate and passed therethrough under the conditions described above. The eluate is discharged from the adsorption zone 80 by a line 82 and will contain not more than about 20 ppm of dissolved molybdenum and, normally, from about 5 to about 15 ppm of dissolved molybdenum.

EXAMPLES

The invention will be illustrated by the following specific examples which are given by way of illustration and not as limitations on the scope of this invention.

Ammonia Pretreatment

The experiments were conducted in a one-liter batch stirred reactor under the conditions as noted in Table II. For example, in Experiment 6547-62, the ammonia was reacted with a molybdenum-containing catalyst solution for one-half hour at 50° C. and a pressure of 50 psig. The reactor was cooled and then vented and the remaining contents filtered. The dried precipitate and the filtrate were analyzed for molybdenum content. In Experiment 6547-62, one part of $NH_3$ (1.0 gram) or 0.0588 mole of ammonia was reacted with six parts (6.0 grams) of a catalyst solution that had a molybdenum content of 0.56 wt. % (6×0.0056, i.e. 0.0336 grams of molybdenum). Since the weight of a gram atom of molybdenum is 95.95 grams, this amounts to 0.00035 gram atoms of molybdenum or a ratio, for Experiment 6547-62, of 168 moles of ammonia per gram atom of molybdenum. For Experiment 6547-62, the dried precipitate was found to contain 55 wt. % of molybdenum and the filtrate was found to contain 52 ppm of molybdenum.

As another example, in Experiment 6270-90, 1 part ammonia was reacted with about 6 parts by weight of a 0.56 wt. % molybdenum catalyst solution (this material was over two years old) at conditions of 100° C., 190 psig. for one hour. The reactor was cooled then vented and the remaining contents filtered. The dried precipitate contained 31 wt. % molybdenum while the filtrate contained 350 ppm molybdenum.

The next six experiments of Table II represented the same recently produced starting material so that the results could be compared directly. In Experiments 6547-63 and 64, gaseous ammonia was used. In Experiments 6547-60, 61, 62 and 66, ammonia and catalyst were charged to the batch stirred reactor. Amounts were added so that the reactor would be about 90% liquid full at operating temperature. It appears that lower levels of molybdenum in the filtrate were achieved with liquid phase reaction of ammonia.

Experiment 6547-62 represented the single stage reaction with ammonia. Experiments 6547-70/76 represented the first and second stage reactions with a more concentrated molybdenum starting material. Molybdenum concentrations are higher in the solid and lower in the filtrate with the single reaction stage as compared to the two stage reaction sequence. Furthermore, milder operating conditions are utilized with the single stage reaction.

When starting materials with higher molybdenum concentrations are reacted with ammonia (Experiments 6547-69 and 73), the filtered solids contained lower molybdenum values whereas the filtrates contained higher levels of molybdenum as compared to a more dilute molybdenum solution starting material.

Experiments 6547-70 and 76 represented a two-stage reaction sequence. In the first stage the molybdenum content was reduced from 15,000 to 3,000 ppm. This filtrate was subjected to a secondary reaction with ammonia in which the level of molybdenum in the filtrate was reduced to 1,900 ppm.

There does not appear to be an advantage in concentrating the molybdenum solution followed by a two-stage reaction sequence over that of a single reaction stage starting with a more dilute molybdenum solution.

TABLE II

| | Reaction of Mo Catalyst Solution with Ammonia | | | | | | |
|---|---|---|---|---|---|---|---|
| Reference | g NH3/ g Cat. Soln. | T (C) | Press (psig) | t (hr) | Init ppm Mo | Precip wt % Mo | Filt ppm Mo |
| 6270-90 | 0.16 | 100 | 190 | 1 | 5,600 | 31 | 350 |
| 6547-63 | 0.21 | 28 | Atm | 1 | 5,600 | 46 | 91 |
| 6547-64 | 0.21 | 55 | Atm | 1 | 5,600 | 50 | 100 |
| 6547-60 | 0.05 | 55 | 25 | 0.5 | 5,600 | 48 | 61 |
| 6547-61 | 0.10 | 50 | 55 | 0.5 | 5,600 | 48 | 70 |
| 6547-62 | 0.16 | 50 | 50 | 0.5 | 5,600 | 55 | 52 |
| 6547-66 | 0.32 | 50 | 200 | 0.5 | 5,600 | 47 | 53 |
| 6547-69 | 0.21 | 200 | 2,600 | 2 | 25,000 | 43 | 2,500 |
| 6547-73 | 0.20 | 180 | 830 | 1 | 18,000 | 44 | 12,000 |
| 6547-70 | 0.40 | 200 | 2,500 | 2 | 15,000 | 42 | 3,000 |
| 6547-76 | 0.83 | 180 | 1,980 | 1 | 3,000 | NES[1] | 1,900 |

[1]Not Enough Sample for Testing

Magnesium Silicate Adsorption

Batch laboratory experiments were conducted in order to illustrate the invention claimed herein.

See Table III. The experiments were conducted in the following way: About 5 parts of catalyst solution to 1 part of adsorbent by weight were mixed together in a beaker, stirred continuously, and held at a temperature of 50–70° C. for one hour. The material was then filtered and the filtrate analyzed for molybdenum content.

In Experiments 6547-78-05 and 79-05 there was no pre-treatment of the catalyst solution. Molybdenum levels were reduced from 5,600 to 1,500 ppm and 430 to <5 ppm, respectively.

The feedstock for Example 6547-85-11 and the feedstock for Example 6547-92-29 was the filtrate recovered after ammonia treatment in Experiment 6547-60 of Table II. The feedstock for Example 6547-85-16 and the feedstock for Example 6547-92-13 was a portion of the filtrate recovered after ammonia treatment in Experiment 6547-61 of Table II. The feedstock for Example 6547-85-21 and the feedstock for Example 6547-93-13 was a portion of the filtrate recovered after ammonia treatment in Experiment 6547-62 of Table II.

The results of the experiments are reported in Table III. Note that when the feedstock for the adsorption step contained from about 50 to 500 ppm of molybdenum, in Experiments 6547-79-05, 6547-85-11, 6547-92-29, 6547-58-16, 6547-92-13, 6547-85-21, and 6547-93-13, satisfactory results were obtained in that the eluate contained not more than about 12 ppm of molybdenum. In contrast, in Experiments 6547-78-05, 6547-93-27, and 6547-94-12 where the feedstock contained in excess of 500 ppm of dissolved molybdenum, unsatisfactory results were obtained in that the eluate contained significantly more than 500 ppm of dissolved molybdenum in the filtrate.

TABLE III

| | Adsorption of Molybdenum | | | |
|---|---|---|---|---|
| Reference | Pre-Treatment | Adsorbent | Initial Mo (ppm) | Eluate[1] Mo (ppm) |
| 6547-78-05 | None | MXL | 5,600 | 1,500 |
| 6547-79-05 | None | MXL | 430 | <5 |
| 6547-85-11 | Ammonia | M | 61 | 7 |
| 6547-92-29 | Ammonia | MXL | 61 | <5 |
| 6547-85-16 | Ammonia | M | 70 | 8 |
| 6547-92-13 | Ammonia | MXL | 70 | <5 |
| 6547-85-21 | Ammonia | M | 52 | 12 |
| 6547-93-13 | Ammonia | MXL | 52 | 9 |
| 6547-93-27 | Ammonia | M | 3,000 | 950 |
| 6547-94-12 | Ammonia | MXL | 3,000 | 800 |

M = Magnesol ®
MXL = Magnesol ® Code XL
[1] After treatment with Magnesol ® or Magnesol ® Code XL brands of adsorbent.

Having thus described our invention, what is claimed is:

1. In a process for the preparation of propylene oxide and tertiary butyl alcohol wherein propylene and tertiary butyl hydroperoxide are reacted in an epoxidation reaction zone in solution in tertiary butyl alcohol in the presence of a soluble molybdenum catalyst to provide an epoxidation reaction product comprising unreacted propylene, unreacted tertiary butyl hydroperoxide, propylene oxide, tertiary butyl alcohol, propylene oxide, dissolved molybdenum catalyst and impurities, including lower aliphatic $C_1$-$C_4$ carboxylic acids, and wherein the epoxidation reaction product is resolved into product fractions in a distillation zone including a distillate propylene fraction, a distillate propylene oxide fraction, a distillate tertiary butyl alcohol fraction and a heavy liquid distillation fraction composed primarily of tertiary butyl hydroperoxide, tertiary butyl alcohol, the dissolved molybdenum catalyst, and impurities, including lower aliphatic $C_1$-$C_4$ carboxylic acids, the improvement which comprises:

a) contacting all or a portion of said heavy distillation fraction which contains from more than about 50 to about 500 ppm of dissolved molybdenum with an effective amount of a solid adsorbent consisting essentially of a synthetic, porous, high surface area amorphous magnesium silicate in an adsorption zone and recovering an eluate from said adsorption zone containing from about 5 to about 20 ppm of dissolved molybdenum.

2. In a process for the preparation of propylene oxide and tertiary butyl alcohol wherein propylene and tertiary butyl hydroperoxide are reacted in an epoxidation reaction zone in solution in tertiary butyl alcohol in the presence of a soluble molybdenum catalyst to provide an epoxidation reaction product comprising unreacted propylene, unreacted tertiary butyl hydroperoxide, propylene oxide, tertiary butyl alcohol, propylene oxide, dissolved molybdenum catalyst and impurities, including lower aliphatic $C_1$-$C_4$ carboxylic acids, and wherein the epoxidation reaction product is resolved into product fractions in a distillation zone including a distillate propylene fraction, a distillate propylene oxide fraction, a distillate tertiary butyl alcohol fraction and a heavy liquid distillation fraction composed primarily of tertiary butyl hydroperoxide, tertiary butyl alcohol, from more than about 500 to about 6,000 ppm of dissolved molybdenum and impurities, including lower aliphatic $C_1$-$C_4$ carboxylic acids, the improvement which comprises:

a) charging said heavy distillation fraction to a precipitation zone and treating said heavy distillation fraction therein with a precipitating agent to form a liquid slurry of a precipitate containing most of the molybdenum initially charged to said precipitation zone, b) separating said precipitate from the liquid portion of said slurry to provide a liquid portion containing from about 50 to about 500 ppm of dissolved molybdenum, and c) contacting said liquid portion with an effective amount of a solid adsorbent consisting essentially of a synthetic, porous, high surface area amorphous magnesium silicate in an adsorption zone and recovering an eluate from said adsorption zone containing from about 5 to about 20 ppm of dissolved molybdenum.

3. A process as in claim 2 wherein the precipitating agent is ammonia.

4. In a process for the preparation of propylene oxide and tertiary butyl alcohol wherein propylene and tertiary butyl hydroperoxide are reacted in an epoxidation reaction zone in solution in tertiary butyl alcohol in the presence of a soluble molybdenum catalyst to provide an epoxidation reaction product comprising unreacted propylene, unreacted tertiary butyl hydroperoxide, propylene oxide, tertiary butyl alcohol, propylene oxide, dissolved molybdenum catalyst and impurities, including lower aliphatic $C_1$-$C_4$ carboxylic acids, and wherein the epoxidation reaction product is resolved into product fractions in a distillation zone including a distillate propylene fraction, a distillate propylene oxide fraction, a distillate tertiary butyl alcohol fraction and a heavy liquid distillation fraction composed primarily of tertiary butyl hydroperoxide, tertiary butyl alcohol, from more than about 500 to about 6,000 ppm of dissolved molybdenum and impurities, including lower aliphatic $C_1$-$C_4$ carboxylic acids, the improvement which comprises:

a) charging said heavy distillation fraction to a precipitation zone and treating said heavy distillation fraction therein with a molar excess of ammonia, as compared with the dissolved molybdenum under precipitation conditions including a temperature of about 20° to about 250° C. and a pressure of about 0 to about 3,000 psig to form a liquid slurry of a precipitate containing most of the molybdenum initially charged to said precipitation zone, b) separating said precipitate from the liquid portion of said slurry to provide a liquid portion containing from about 50 to about 500 ppm of dissolved molybdenum, and c) contacting said liquid portion with an effective amount of a solid adsorbent consisting essentially of a synthetic, porous, high surface area amorphous magnesium silicate in an adsorption zone and recovering an eluate from said adsorption zone containing from about 5 to about 20 ppm of dissolved molybdenum.

* * * * *